United States Patent [19]

Alpegiani et al.

[11] Patent Number: 5,356,888
[45] Date of Patent: Oct. 18, 1994

[54] 1,1-DIOXO-CEPHEM-4-CARBOTHIOLIC ACID DERIVATIVES

[75] Inventors: Marco Alpegiani, Milan; Pierluigi Bissolino, San Giorgio di Lomellina; Ettore Perrone, Boffalora Ticino; Francesco Di Matteo; Piergiuseppe Orezzi, both of Milan; Giuseppe Cassinelli, Voghera, all of Italy

[73] Assignee: Farmitalia Carlo Erba, Milan, Italy

[21] Appl. No.: 780,549

[22] Filed: Oct. 22, 1991

Related U.S. Application Data

[63] Continuation of Ser. No. 457,812, Jan. 12, 1990, abandoned.

[30] Foreign Application Priority Data

May 13, 1988 [GB] United Kingdom ............ 8811388.1

[51] Int. Cl.$^5$ ................ C07D 501/20; A61K 31/545
[52] U.S. Cl. .................... 514/204; 514/200; 514/203; 540/221; 540/222; 540/225; 540/226
[58] Field of Search ............. 540/215, 230, 221, 222, 540/226, 225; 514/200, 201, 202, 203

[56] References Cited

U.S. PATENT DOCUMENTS

| | | | |
|---|---|---|---|
| 4,547,371 | 10/1985 | Doherty et al. | 540/230 |
| 4,547,371 | 10/1985 | Doherty et al. | 540/230 |
| 4,623,645 | 11/1986 | Doherty et al. | |
| 5,077,286 | 12/1991 | Bissolino et al. | 540/227 |
| 5,258,377 | 11/1993 | Maiti et al. | 514/201 |

FOREIGN PATENT DOCUMENTS

| | | |
|---|---|---|
| 0124081 | 11/1984 | European Pat. Off. |
| 0207447 | 1/1987 | European Pat. Off. |
| 0267723 | 5/1988 | European Pat. Off. |
| 1187323 | 4/1970 | United Kingdom |

OTHER PUBLICATIONS

Chemical Abstracts, vol. 89, No. 23, 4 Dec. 1978 (Columbus, Ohio, US), R. Matsueda: "A mild and efficient method for the esterification of cephalosporanic acids", see p. 621, abstract No. 197431h, & Chem. Lett. 1978, (9), 979–82.

*The Journal of Antibiotics*, (1985), 38, pp. 1273–1276, "Cephalosporins Containing Carbohydrates", Miskolci et al.

Primary Examiner—Nicholas Rizzo
Attorney, Agent, or Firm—Oblon, Spivak, McClelland, Maier & Neustadt

[57] ABSTRACT

There are provided compounds I

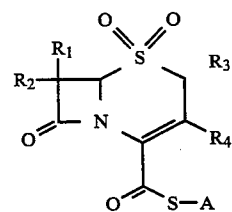

wherein
  A is a hydrogen atom or an organic group,
  $R_1$ is hydrogen or halogen atom or an organic group,
  $R_2$ is hydrogen or halogen atom, $C_1$–$C_4$ alkyl or acyloxy group,
  $R_3$ is hydrogen atom, $C_1$–$C_4$ alkyl or alkoxy, benzyl group or a methylene and
  $R_4$ is chloro, fluoro, hydrogen atom or an organic group.

The compounds I are elastase inhibitors. A process for their preparation is also provided, as are pharmaceutical compositions containing them.

18 Claims, No Drawings

1,1-DIOXO-CEPHEM-4-CARBOTHIOLIC ACID DERIVATIVES

This application is a continuation of application Ser. No. 07/457,812, field on Jan. 12, 1990, now abandoned.

The invention relates to 8-oxo-5-thia-1-azabicyclo[4,2,0]-oct-2-ene-5,5-dioxide-2-carbothiolic acids, to a process for their preparation, and to pharmaceutical and veterinary preparations containing them. The compounds according to the invention are useful as protease inhibitors, especially human leukocyte elastase (HLE) inhibitors, and for the prevention, control and treatment of inflammatory and degenerative diseases caused by proteolytic enzymes, in particular emphysema, adult respiratory distress syndrome, rheumatoid arthritis, osteroarthritis, infectious arthritis, rheumatic fever, spondylitis, gout, lupus and psoriasis.

In this Specification, the following abbreviations are used:
Ac: acetyl,
Boc: t-butoxycarbonyl,
Cbz: benzoxycarbonyl,
Suc: 3-carboxypropionyl,
Glu: 4-carboxybutyryl, and
NPG: an amino protecting group selected from the above.

The Invention provides compounds of the general formula (I):

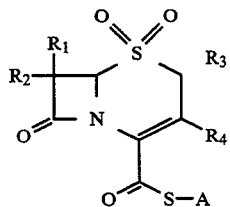

I wherein
A represents
(a) a hydrogen atom,
(b) a straight chain or branched chain alkyl group having from 1 to 20 carbon atoms,
(c) a straight chain or branched chain alkenyl group having from 2 to 10 carbon atoms,
(d) a straight chain or branched chain alkynyl group having from 2 to 10 carbon atoms,
(e) an aryl group having from 6 to 10 carbon atoms,
(f) a cycloalkyl group being of monocyclic, bicyclic or bridged ring form and having from 3 to 10 carbon atoms,
(g) a cyctoalkenyl group having from 5 to 8 carbon atoms,
(h) an aralkyl group in which the aryl part is as defined in (e) above and the alkyl part is as defined in (b) above,
(j) an aralkenyl group in which the aryl part is as defined in (e) above, and the alkenyl part is as defined in (c) above,
(k) an aralkynyl group in which the aryl part is as defined in (e) above and the alkynyl part is as defined in (d) above,
(l) a cycloalkylalkyl group in which the cyclcoalkyl part is as defined in (f) above and the alkyl part is as defined in (b) above,
(m) a heterocyclyl group, saturated or unsaturated, having 5 or 6 ring atoms of which at least one is an oxygen, sulphur or nitrogen atom, optionally fused with a second such heterocyclyl group which may be the same or different or with a cycloalkyl group as defined in (f) above,
(n) a heterocyclylalkyl group in which the heterocyclyl part is as defined in (m) above and the alkyl part is as defined in (b) above,
(o) a heterocyclylalkenyl group in which the heterocyclyl part is as defined in (m) above and the alkenyl part is as defined in (c) above, or
(p) a heterocyclylalkynyl group in which the heterocyclyl part is as defined in (m) above and the alkynyl part is as defined in (d) above, each of the groups defined in (b) to (p) above being unsubstituted or substituted by one or more of
(i) a halogen atom,
(ii) a nitro, azido, diazo, amino or guanidino group or a group of the formula $NHR_1$, $NR_aR_b$, $NHCOR_c$, $NHCOOR_c$ or $NHSO_2R_a$ wherein each of $R_a$ and $R_b$ independently represents a straight chain or branched chain alkyl group having from 1 to 7 carbon atoms, optionally substituted by a carboxy group, a phenyl group or a benzyl group and $R_c$ represents a 2-carboxyethyl or 3-carboxypropyl group or any of the groups which $R_a$ may represent,
(iii) a t-butyldiphenylsilyloxy group or a group of the formula $OR_d$, $OCOR_d$, $OCOOR_d$ or $OCONHR_d$ wherein $R_d$ represents a hydrogen atom, a 2-carboxy-2-aminoethyl or diphenylmethyl group or any of the groups which $R_c$ may represent,
(iv) a mercapto or sulpho group or a group of the formula $SR_a$, $SOR_a$ or $SO_2R_a$ wherein $R_a$ is as above defined,
(v) a cyano or trifluoroacetyl group or a group of the formula

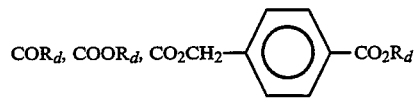

or $CONHR_d$ wherein $R_d$ is as above defined, or
(vi) as a ring substituent only, a straight chain or branched chain alkyl, alkenyl or alkynyl group each of which has up to 4 carbon atoms and is optionally substituted by a carboxy group or a cycloalkyl group having from 3 to 6 carbon atoms:

$R_1$ represents
(1) a fluorine, chlorine, bromine or iodine atom,
(2) a group A as above defined,
(3) a group OA wherein A is as above defined,
(4) a group SA, SOA or $SO_2A$ wherein A is as above defined,
(5) a group OCOA wherein A is as above defined,
(6) a group $OSO_2A$ wherein A is as above defined, or
(7) a group NHCOA or NHZ wherein A is as above defined and Z represents a mono-, di- or or protected by a group $COR_c$ or $COOR_c$ wherein tripeptide, constituted by D or L α-aminoacids chosen from Ala, Gly, Val, Leu, Ile, Phe and Pro, with the terminal amino group either free or protected by a group $COR_c$ or $COOR_c$ wherein $R_c$ is as above defined;

$R_2$ represents a hydrogen, fluorine, chlorine or bromine atom, a straight chain or branched chain alkyl group having from 1 to 4 carbon atoms, a formyloxy group or an alkanoyloxy group having from 2 to 5 carbon atoms:

$R_3$ represents a hydrogen atom, a straight chain or branched chain alkyl group having from 1 to 4 carbon atoms, a benzyl group or a group of the formula $=CHR_e$ wherein $R_e$ represents a hydrogen atom, a straight chain or branched chain alkyl group having from 1 to 4 carbon atoms, a phenyl or carboxy group an alkoxy or alkoxycarbonyl group having from 1 to 5 carbon atoms or a benzyloxycarbonyl group; and $R_4$ represents (1) a group A as above defined,
(2) a fluorine or chlorine atom,
(3) a group OA wherein A is as above defined,
(4) a group SA, SOA or $SO_2A$ wherein A is as above defined,
(5) a group COA or COOA wherein A is as above defined,
(6) a group $CH_2OA$ wherein A is as above defined,
(7) a group $CH_2SA$, $CH_2SOA$ or $CH_2SO_2A$ wherein A is as above defined,
(8) a group $CH_2OCOA$ or $CH_2OZ$ wherein A and Z are as above defined,
(9) a group $CH_2S.COA$ wherein A is as above defined,
(10) a group $CH_2NAA'$ wherein either A is as above defined and A' independently from A represents any of the groups which A may represent, or $NAA'$ represents a heterocyclic ring,
(11) a group $CH_2+AA'A''$ wherein either A and A' are as above defined and A'' independently from A represents any of the groups which A may represent, or $NA'A''$ represents an aromatic heterocyclic ring substituted by the group A as above defined or by a carbamoyl group, or
(12) a group $CH_2NHCOA$ or $CH_2NHZ$ wherein A and Z are as above defined.

The compounds of the general formula I may contain one or more ionic or ionizable groups. In this instance, the salts of such compounds with pharmaceutically acceptable anions or cations are included within the scope of the invention.

The invention encompasses all the possible stereoisomers, as well as their racemic or optically active mixtures, of the compounds of the general formula I. However, the configuration depicted in the general formula Ia is particularly preferred:

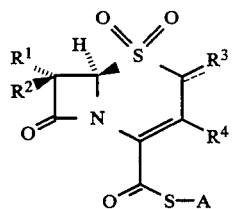

(Ia)

Preferably A represents
(a') a hydrogen atom, (b') a straight chain or branched chain alkyl group having from 1 to 20 carbon atoms, such as $C_1$-$C_{10}$ alkyl or $C_1$-$C_6$ alkyl,
(e') a phenyl or naphthyl group,
(f') a cycloalkyl group being of monocyclic, bicyclic or bridged ring form and having from 3 to 10 carbon atoms, such as monocyclic $C_3$ to $C_7$ cycloalkyl, for example $C_3$, $C_5$, $C_6$ or $C_7$ cycloalkyl,
(h') a phenylalkyl or naphthylalkyl group in which the alkyl part is as defined in (b') above,
(l') a cycloalkylalkyl group in which the cycloalkyl part is as defined in (f') above and the alkyl part is as defined in (b') above,
(m') a heterocyclyl group, saturated or unsaturated, having 5 or 6 ring atoms of which at least one is an oxygen, sulphur or nitrogen atom, or
(n') a heterocyclylalkyl group in which the heterocyclyl part is as defined in (m') above and the alkyl part is as defined in (b') above.

Each of the groups defined in (b') to (n') above is preferably unsubstituted or substituted by one or more of (i') a halogen atom,
a nitro, amino or guanidino group or a group of
(ii') a nitro, amino or guanidino group or a group of the formula $NHR_e$, $NR_eR_f$, $NHCOR_g$, $NHCOOR_g$ or $NHSO_2R_e$ wherein each of $R_e$ and $R_f$ independently represents a straight chain or branched chain alkyl group having from 3 to 7 carbon atoms, a phenyl group or a benzyl group and $R_g$ represents a 2-carboxyethyl or 3-carboxypropyl group or any of the groups which $R_e$ may represent,
(iii') a t-butyldiphenylsilyloxy group or a group of the formula $OR_d$, $OCOR_d$ $OCOOR_d$ or $OCONHR_d$ wherein $R_d$ represents a hydrogen atom, a 2-carboxy-2-aminoethyl or diphenylmethyl group or any of the groups which $R_c$ may represent,
(iv') a group of the formula $SR_a$, $SOR_a$ or $SO_2R_a$ wherein $R_a$ is as above defined
(v') a cyano or trifluoroacetyl group or a group of the formula

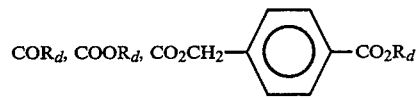

or $CONHR_d$ wherein $R_d$ is as above defined; or
(vi') as a ring substituent only, a straight chain or branched chain alkyl group having from 1 to 4 carbon atoms.

Most preferably, A represents a hydrogen atom or a methyl, ethyl, propyl, isopropyl, butyl, s-butyl, t-butyl, pentyl, neopentyl, hexyl, cyclopropyl, cyclopentyl, cyclohexyl, adamantyl, phenyl, benzyl, naphthyl, o-tolyl, o,o-xylyl, diphenylmethyl, trityl, 1-phenyl-2-propyl, 1-phenylethyl, phenethyl, 4-carboxybenzyl, 3-carboxybenzyl, carboxymethyl, 1-carboxyethyl, 2-carboxypropyl, 4-carboxyphenyl, hydroxyethyl, 2-(t-butoxy)-ethyl, 2-pivaloyloxyethyl, 2-acetoxyethyl, 2-pyridiniumethyl, 4-methoxyphenyl, 2-pyridyl, 2-(3-carboxypropionyloxy)-ethyl, 2-carboxymethoxy-ethyl, 2-(carboxyethylcarbamoyloxy)-ethyl, 2-(3-carboxy-3-aminopropionyloxy)-ethyl, 2-carboxy-2-aminoethyl, 3-carboxy-3-aminopropyl, 2-carboxy-2-amino-l-methylethyl, 4-(t-butoxycarbonyl)-benzyl, t-butyldiphenylsilyloxyethyl, 2-diphenylmethoxycarbonyl- 2-(t-butoxycarbonylamino)-ethyl, 2-(t-butoxycarbonylamino)-2-carboxyethyl, t-butoxycarbonylmethyl or diphenylmethoxycarbonyloxyethyl; 2-t-butoxycarbonylbenzyloxy-2-(t-butoxycarbonylamino)-ethyl, 2-carboxybenzyloxy-2-(t-butoxycarbonylamino)-ethyl or 2-(t-butoxycarbonylamino)-2-t-butoxycarbonyl-ethyl group.

Preferably $R_1$ represents
(1') a fluorine, chlorine or bromine atom,
(2') a hydrogen atom, a straight chain or branched chain alkyl group having from 1 to 4 carbon atoms, or a 1-hydroxyethyl, 1-benzoxyethyl, 1-benzoxycarbonyloxyethyl, 1-phenylacetoxyethyl 2-fluoro-1-hydroxyethyl, phenyl or benzyl group,
(3') a methoxy, ethoxy, isopropoxy, phenoxy or benzoxy group,
(4') a methylthio group,
(5') a formyloxy, acetoxy or phenylacetoxy group,
(6') a mesyl or tosyloxy group, or
(7') a formamido, acetamido, fluoroacetamido, trifluoroacetamido or chloroacetamido group, or a group NH-Ala, NH-Val, NH-Pro-Val, NH-Lys or NH-Pro-Ala-Ala with the terminal amino group either free or protected by an Ac, Boc, CBz or Suc group.

Most preferably $R_1$ represents
(1'') a fluorine, chlorine or bromine atom
(2'') a methyl, ethyl, 1-hydroxyethyl, 1-benzoxyethyl, 1-benzoxycarbonyloxyethyl or 1-phenylacetoxyethyl group
(3'') a methoxy group, or
(7'') a formamido, acetamido or trifluoroacetamido group or a group NH-Ala, NH-Ala (Ac), NH-Val (Suc), NH-L-Pro-L-Val, NH-Lys (Suc), NH-Pro-Ala-Ala or NH-Pro-Ala-Ala(Ac).

$R_2$ preferably represents a hydrogen, fluorine or chlorine atom, most-preferably a hydrogen atom.

$R_3$ preferably represents a hydrogen atom or a methyl or benzyl, benzyloxycarbonylmethylene or carboxymethylene group, most preferably a hydrogen atom or a methyl group.

Preferably $R_4$ represents
(1') a hydrogen atom or a methyl, chloromethyl, bromomethyl or benzyl group,
(2') a chlorine atom,
(3') a methoxy or benzoxy group,
(4') a methylthio group,
(5') a formyl, acetyl, benzoyl, carboxy, methoxycarbonyl, ethoxycarbonyl, t-butoxycarbonyl or benzoxycarbonyl group,
(6') a methoxymethyl, ethoxymethyl or isopropoxymethyl group: or a benzoxymethyl, phenoxymethyl or 3-pyridyloxymethyl group in each of which the ring is either unsubstituted or is substituted by one or two equal or different groups chosen from hydroxy, carboxy and amino groups and alkoxycarbonyl groups having from 2 to 5 carbon atoms,
(7') a methylthiomethyl, phenylthiomethyl, methylsulphonylmethyl, phenylsulphonylmethyl or phenylsulphinylmethyl group, or a 2-amino-2-carboxyethylthiomethyl group in which the amino group is either free or protected with an Ac, Boc or Cbz group and the carboxy group is either free or protected with an ethyl, t-butyl, benzyl, methyl or diphenylmethyl group: or a group CH₂SHet in which Het represents an optionally substituted heterocyclic group, especially one of the formula

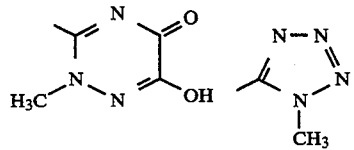

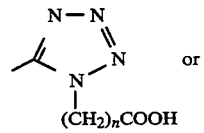

wherein may be 1, 2 or 3;

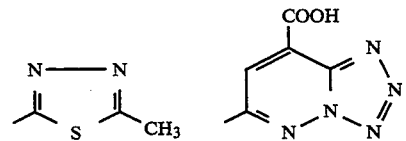

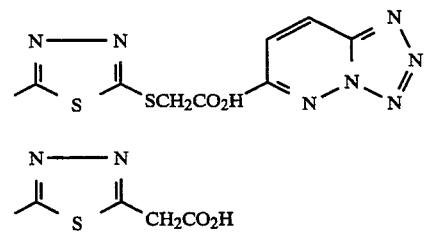

(8') a benzoyloxymethyl or phenylacetoxymethyl group or an alkanoyloxymethyl group having from 3 to 10 carbon atoms; each of which may be unsubstituted or substituted by one or two equal or different groups chosen from carboxy, hydroxy and amino groups, any amino group being free or protected by NPG, or a group CH₂-O-Pro-Val in which the amino group is either free or protected with an Ac, Boc or Cbz group,
(9') an acetylthiomethyl group,
(10') an aminomethyl group or a group CH₂NHR$_k$ wherein R$_k$ represents a straight chain or branched chain alkyl group having from 1 to 4 carbon atoms, unsubstituted or substituted by a carboxy group; especially a group —CH₂—Ala, —CH₂—Gly or —CH₂—Val,
(11') a group CH₂+NR$_m$R$_n$R$_o$ wherein each of R$_m$, R$_n$ and R$_o$ independently has any of the values of R$_k$ as above defined: a group of the formula

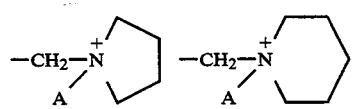

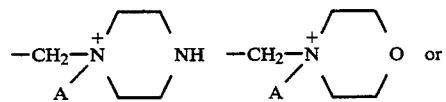

-continued

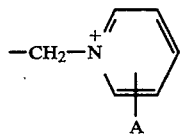

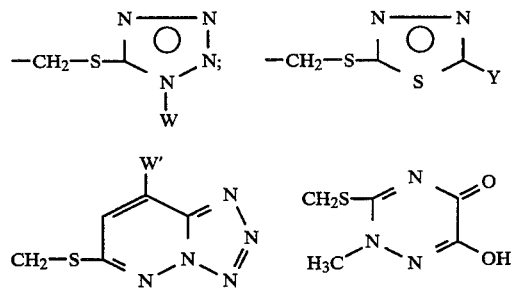

wherein A is as above defined: a 4-carbamoylpyridiniummethyl group: or a quinuclidiniummethyl group, optionally substituted by a group A as above defined or by a carbamoyl group, (12′) an acetylaminomethyl or benzoylaminomethyl group or a group $CH_2$—NH—Ala, $CH_2$—NH—Val, $CH_2$—NH—Pro, $CH_2$—NH—Phe, $CH_2$—NH—Pro—Val, $CH_2$—NH—Ala—Ala or $CH_2$NH—Pro—Ala in which the amino group is either free or protected with NPG.

$R_4$ most preferably represents a methyl, bromomethyl, acetoxymethyl, hydroxymethyl, carbamoyloxymethyl, methoxymethyl, phenoxymethyl, aminomethyl, pyridiniummethyl, 4-carboxymethylpyrldiniummethyl, benzoyloxymethyl, benzoxymethyl. 3-pyridyloxymethyl. phenacetoxymethyl, methylsulphonylmethyl, phenylsulphinylmethyl, 3-carboxypropionyloxymethyl, 4-carboxybenzoyloxymethyl, 4-(t-butoxycarbonyl)-benzoyloxymethyl. N-(carboxymethyl)carbamoyloxymethyl or (1-carboxy-2-methylpropylamino)methyl group; a group $CH_2$NH—Val: a group $CH_2$-O-Val, $CH_2$—O—Ala, $CH_2$—O—Gly or $CH_2$—O—Pro—Val or an Ac, Boc or Cbz protected derivative of such a group: a group $CH_2$—O—Ala(-Glu): a group $CH_2$—OCONH—$CH(R_p)$COOH wherein $R_p$ represents a straight chain or branched chain alkyl group having from 3 to 7 carbon atoms or a phenyl group; a group in which W represents hydrogen atom methyl or $(CH_2)_nCO_2H$ group, n is as defined above, Y represents a methyl, carboxymethylthio or carboxymethyl group and W' represents hydrogen atom or carboxy group; or a group

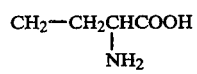

or its Ac Boc or Cbz protected derivative and/or its methyl, ethyl, t-butyl, benzyl or diphenylmethyl ester.

Specific examples of the preferred compounds of the invention are those listed below:

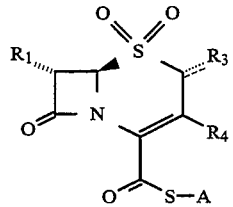

| No. | A | $R^1$ | $R^3$ | $R^4$ |
|---|---|---|---|---|
| 1 | 4-methoxyphenyl | Cl | H | $CH_2OCOCH_3$ |
| 2 | n-$C_4H_9$ | ″ | ″ | ″ |
| 3 | t-$C_4H_9$ | ″ | ″ | ″ |
| 4 | $CH(CH_3)_2$ | ″ | ″ | ″ |
| 5 | H | ″ | ″ | ″ |
| 6 | $CH_3$ | ″ | ″ | ″ |
| 7 | $C_2H_5$ | ″ | ″ | ″ |
| 8 | $CH_2CH_2CH_3$ | ″ | ″ | ″ |
| 9 | $CH(CH_3)C_2H_5$ | ″ | ″ | ″ |
| 10 | cyclohexyl | ″ | ″ | ″ |
| 11 | $CH_2C_6H_5$ | ″ | ″ | ″ |
| 12 | $(CH_2)_5CH_3$ | ″ | ″ | ″ |
| 13 | $CH(CH_3)C_6H_5$ | ″ | ″ | ″ |
| 14 | $C(CH_3)_2C_6H_5$ | ″ | ″ | ″ |
| 15 | $CH_2CH_2C_6H_5$ | ″ | ″ | ″ |
| 16 | 4-carboxybenzyl | ″ | ″ | ″ |
| 17 | 4-(t-butoxycarbonyl)-benzyl | ″ | ″ | ″ |
| 18 | cyclopropyl | ″ | ″ | ″ |
| 19 | $CH_2CH_2OH$ | ″ | ″ | ″ |
| 20 | $CH_2CH_2OC(O)^tC_4H_9$ | ″ | ″ | ″ |
| 21 | 2-pyridiniumethyl chloride | ″ | ″ | ″ |
| 22 | $CH_2CO_2H$ | ″ | ″ | ″ |
| 23 | $CH_2CO_2{}^tC_4H_9$ | ″ | ″ | ″ |
| 24 | $CH(CH_3)CO_2H$ | ″ | ″ | ″ |
| 25 | 2-pyridyl | ″ | ″ | ″ |
| 26 | o-tolyl | ″ | ″ | ″ |
| 27 | 2,6-xylyl | ″ | ″ | ″ |
| 28 | $CH(C_6H_5)_2$ | ″ | ″ | ″ |
| 29 | $C(C_6H_5)_3$ | ″ | ″ | ″ |
| 30 | $CH_2CH_2OC(O)CH_2CH_2CO_2H$ | ″ | ″ | ″ |
| 31 | $CH_2CH_2OCH_2CO_2H$ | ″ | ″ | ″ |
| 32 | $CH_2CH_2OCONHCH_2CH_2CO_2H$ | Cl | H | $CH_2OCOCH_3$ |

-continued

| No. | A | R¹ | R³ | R⁴ |
|---|---|---|---|---|
| 33 | CH₂CH₂OC(O)CH₂CH(NH₂)CO₂H | ″ | ″ | ″ |
| 34 | CH₂CH(NH₂)CO₂H | ″ | ″ | ″ |
| 35 | CH₂CH(NHCO₂ᵗBu)CO₂H | ″ | ″ | ″ |
| 36 | CH₂CH₂CH(NH₂)CO₂H | ″ | ″ | ″ |
| 37 | CH(CH₃)CH(NH₂)CO₂H | ″ | ″ | ″ |
| 38 | t-C₄H₉ | OCH₃ | ″ | ″ |
| 39 | 4-carboxybenzyl | ″ | ″ | ″ |
| 40 | benzyl | ″ | ″ | ″ |
| 41 | t-C₄H₉ | Cl | ″ | CH₂S(O)Ph |
| 42 | ″ | ″ | ″ | 3-pyridyloxy-methyl |
| 43 | ″ | ″ | ″ | CH₂OCO Ph |
| 44 | ″ | ″ | ″ | 4-carboxy-benzyloxy-methyl |
| 45 | ″ | ″ | ″ | CH₂OC(O)CH₂CH₂CO₂H |
| 46 | ″ | ″ | ″ | CH₂OCOCH₂Ph |
| 47 | ″ | ″ | ″ | CH₂OC(O)CH₂NH₂ |
| 48 | ″ | ″ | ″ | CH₂OC(O)CH₂NHCO₂ᵗBu |
| 49 | ″ | ″ | ″ | CH₂OC(O)CH(NH₂)CH(CH₃)₂ |
| 50 | ″ | ″ | ″ | CH₂OCONHCH₂CO₂H |
| 51 | ″ | ″ | ″ | CH₂OC(O)CH(NH₂)CH₃ |
| 52 | ″ | ″ | ″ | CH₂OC(O)CH(NHCO₂ᵗBu)CH₃ |
| 53 | ″ | ″ | ″ | CH₂OC(O)CH(NH₂)CH₂CO₂H |
| 54 | ″ | ″ | CH₃ | CH₂OCOCH₃ |
| 55 | CH₂CH₂OSiᵗBuPh₂ | ″ | H | CH₂OCOCH₃ |
| 56 | CH₂CO₂CHPh₂ | ″ | ″ | ″ |
| 57 | CH₂CH(NHCO₂ᵗC₄H₉)CO₂CHPh₂ | ″ | ″ | ″ |
| 58 | t-C₄H₉ | Cl | H | CH₃ |
| 59 | ″ | ″ | ″ | CH₂OCH₃ |
| 60 | ″ | ″ | ″ | 5-(methylthio)-1-methyl-1H-tetrazol-yl-methyl |
| 61 | ″ | OCH₃ | ″ | ″ |
| 62 | ″ | H | ″ | ″ |
| 63 | ″ | OCH₃ | =CH—CO₂CH₂Ph | CH₃ |
| 64 | ″ | Cl | ″ | ″ |
| 65 | ″ | ″ | =CH—CO₂H | ″ |
| 66 | ″ | OCH₃ | ″ | CH₂OCOCH₃ |
| 67 | ″ | ″ | H | 3-(methylthio)-1-methyl-6-hydroxy-5-oxo-1,2,4-triazinyl-methyl |
| 68 | ″ | ″ | ″ | 5-(methylthio)-1-(carboxymethyl)-1H-tetrazol-yl-methyl |
| 69 | ″ | ″ | ″ | CH₂OCONH₂ |
| 70 | ″ | ″ | ″ | COOH |
| 71 | ″ | ″ | ″ | 2-(methylthio)-5-(carboxymethylthio)-1,3,4-thiadiazolyl |
| 72 | ″ | ″ | CH₃ | CH₂OCOCH₃ |

-continued

| No. | A | R$^1$ | R$^3$ | R$^4$ |
|---|---|---|---|---|
| 73 | " | " | OCH$_3$ | ![structure: CH$_2$-S-C(=N-N(CH$_3$))-... triazine ring with =O and OH] |
| 74 | −CH$_2$CH(NHCOO-t-C$_4$H$_9$)−COOH | OCH$_3$ | H | ![structure: −CH$_2$−S− thiadiazole with N−CH$_3$] |
| 75 | " | " | " | ![structure: CH$_3$−N−N= triazine with =O, OH and CH$_2$−S−] |
| 76 | −CH$_2$CH(NHCOO-t-C$_4$H$_9$)COO-t-C$_4$H$_9$ | " | " | " |
| 77 | " | " | " | ![structure: −CH$_2$−S− tetrazole with −CH$_2$COOH] |
| 78 | " | " | " | ![structure: −CH$_2$−S−C(=N−N=)−S−(thiadiazole with SCH$_2$COOH)] |
| 79 | −CH$_2$CH(NHCOO-t-C$_4$H$_9$)COOCH$_2$−C$_6$H$_4$−COO-t-C$_4$H$_9$ | " | " | " |
| 80 | " | " | " | ![structure: −CH$_2$−S− tetrazole with −CH$_2$COOH] |
| 81 | " | " | " | ![structure: CH$_3$−N−N triazine with CH$_2$−S−, =O, OH] |
| 82 | −CH$_2$CH(NHCOO-t-C$_4$H$_9$)COOCH$_2$−C$_6$H$_4$−COOH | " | " | " |
| 83 | " | " | " | ![structure: −CH$_2$−S− tetrazole with N−CH$_3$] |

-continued

| No. | A | R¹ | R³ | R⁴ |
|---|---|---|---|---|
| 84 | " | " | " | ![structure: -CH₂-S-(1,2,3,4-oxatriazole ring)-CH₂COOH] |
| 85 | " | " | " | ![structure: -CH₂-S-(1,3,4-thiadiazole with O)-SCH₂COOH] |
| 86 | " | " | " | ![structure: -CH₂-S-(1,3,4-thiadiazole with O)-CH₂COOH] |
| 87 | " | " | " | ![structure: -CH₂-S-(1,3,4-thiadiazole)-CH₃] |
| 88 | " | " | " | ![structure: -CH₂-S-(triazole with O)-(CH₂)₃COOH] |
| 89 | —CH₂CHCOOH<br>     \|<br>   NHCOO-t-C₄H₉ | OCH₃ | H | ![structure: CH₂-S-(triazole with O)-(CH₂)₃COOH] |
| 90 | —CH₂CHCOO-t-C₄H₉<br>     \|<br>   NHCOO-t-C₄H₉ | " | " | " |
| 91 | —CH₂CHCOOCH₂—⟨phenyl⟩—COO-t-C₄H₉<br>     \|<br>   NHCOO-t-C₄H₉ | " | " | " |
| 92 | —CH₂CHCOOCH₂—⟨phenyl⟩—COO-t-C₄H₉<br>     \|<br>   NHCOO-t-C₄H₉ | OCH₃ | H | ![structure: CH₂-S-(1,3,4-thiadiazole)-CH₃] |
| 93 | —CH₂CHCOOH<br>     \|<br>   NHCOO-t-C₄H₉ | " | " | " |
| 94 | —CH₂CHCOO-t-C₄H₉<br>     \|<br>   NHCOO-t-C₄H₉ | " | " | " |
| 95 | —CH₂CHCOOCH₂—⟨phenyl⟩—COO-t-C₄H₉<br>     \|<br>   NHCOO-t-C₄H₉ | " | " | " |
| 96 | —CH₂CHCOOH<br>     \|<br>   NHCCH₃<br>     \|\|<br>     O | " | " | " |

| No. | A | R¹ | R³ | R⁴ |
|---|---|---|---|---|
| 97 | —CH₂CH(NHCOCH₃)COOCH₂-C₆H₄-COOH | " | " | " |
| 98 | " | " | " | —CH₂—S—[5-(1-methyl-1,3,4-oxadiazol-2-yl)] (tetrazole-oxadiazole ring) |
| 99 | —CH₂CH(NHCOCH₃)COOH | " | " | " |
| 100 | —CH₂CH(NHCOCH₃)COO-t-C₄H₉ | " | " | —CH₂—S—[6-hydroxy-5-oxo-4-methyl-1,2,4-triazin-3-yl] |
| 101 | " | " | " | —CH₂—S—[1-(3-carboxypropyl)-1,3,4-oxadiazol-2-yl] ring with (CH₂)₃COOH |
| 102 | —CH₂CH(NHCOCH₃)COOCH₂CH₃ | " | " | " |
| 103 | —CH₂CH(NHCOCH₃)—CON(pyrrolidine) | OCH₃ | H | tetrazolo[1,5-b]pyridazine with CO₂H and CH₂S |
| 104 | —CH₂CH[NHCOC(CH₃)₃]CON(pyrrolidine) | OCH₃ | H | CH₂S—oxadiazole with (CH₂)₃CO₂H |
| 105 | —CH₂CH(NHCOO-t-C₄H₉)CO₂CHPh₂ | OCH₃ | H | CH₂S—oxadiazole with CH₃ |
| 106 | —CH₂CH(NHCOO-t-C₄H₉)CO₂CHPh₂ | OCH₃ | H | CH₂S—oxadiazole with (CH₂)₃CO₂H |

The invention further provides a method for the preparation of a compound of the general formula I, the method commencing from a compound of the general formula II

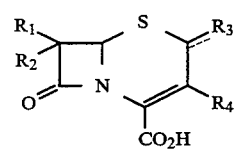

(II)

wherein $R_1$, $R_2$, $R_3$, $R_4$ are as defined above, and comprising the steps of:

converting the carboxy group at the 4-position of the cephem nucleus into a group of the formula —C(=O)SA wherein A is as defined above: and oxidising the sulphur atom at the 1-position of the cephem nucleus to the sulphone oxidation level, the steps being carried out in either order.

In the conversion step, the acids are converted into their thioesters by reaction with a mercaptan, or a derivative thereof, having the general formula III

X—S—A  (III)

wherein A is as above defined and X represents a hydrogen atom, a metal, preferably thallium (I), copper (I), silver, sodium or lithium or a boryl, stannyl or sulphenyl residue.

In this reaction, prior or in situ activation of the carboxylic acids may be necessary or desired. Examples of prior activation are the conversion of carboxylic acids into their acid chlorides, anhydrides, or mixed anhydrides with carboxylic acids (e.g. by reaction with pivaloyl chloride), carbonic acid derivatives (e.g. by reaction with haloformates, such as ethyl chloroformate), sulphonic acids (e.g. by reaction with mesyl chloride or tosyl chloride), and phosphonic acid derivatives (e.g. by reaction with diphenyl chlorophosphate, diethylchlorophosphate, phenyldichlorophosphate, N,N-dimethylphosphoramidic dichloride, diethylphosphoryl cyanide or diphenylphosphonylazide). Examples of in situ activation are the presence the reaction mixture of about one molar equivalent of a carbodiimide (e.g. dicyclohexyl carbodiimide), or of 1-hydroxybenzotriazole and dicyclohexylcarbodiimide, or the presence of a large excess of polyphosphate ester (PPE, prepared according to W. Pollman, G. Schramm, Biochem. Biophys. Acta 80, 1 (1964)). General conditions for these activations/conversions are known: see, for example, E. Haslam, "Recent Developments in Methods for the Esterification and Protection of the Carboxyl groups", Tetrahedron 36, 2409 (1980). Suitable solvents are organic, aprotic, polar or apolar solvents such as dichloromethane, chloroform, tetrahydrofuran, acetonitrile, diethyl ether, benzene, dimethylformamide, dimethylsulphoxide, pyridine and ethyl acetate; suitable reaction temperatures are in the range of −78° C. to +80° C., preferably from −30° C. to room temperature.

When in the reagent of the general formula III X is a boryl residue, such reagent, generally known as "trisalkylthio borane" (III′)

(A—S)₂B—S—A  (III)′ wherein A is as defined above, reacts with the (unactivated) carboxylic acids to give the corresponding thioesters by simple reflux in an inert organic solvent such as benzene or diethyl ether.

When in the reagent of the general formula III X is a stannyl residue, such reagent, generally known as "organotin mercaptide" (III″)

(Alk)₃ Sn—S—A  (III″)

wherein A is as defined above, and Alk is an alkyl residue (preferably n-butyl), reacts with the carboxylic acids, after their prior activation to the corresponding acid chlorides, in an organic solvent, such as chloroform, at temperatures ranging from about 0° C. to about 80° C.

When in the reagent of formula (III) X is a sulphenyl residue, such reagent, known as a "disulphide" (III‴)

AS—S—A  (III‴)

wherein A is defined above, reacts with the (unactivated) carboxylic acids in the presence of about one molar equivalent of triphenylphosphine. This reaction is conveniently run when A is an aryl or heterocyclyl residue, as above defined, in an organic solvent, such as benzene, chloroform or acetone, at temperatures ranging from approx 10° C. to approx. 90° C.

General chemical details for the above-said methods for thioester formation can be found in the literature e.g. see J. Chem. Soc., Chem. Commun. 1969, 435 (for the reaction of trisalkylthioboranes): Tetrahedron Lett. 31, 979, 2853 (for the reaction of organotin mercaptides); Bull. Chem. Soc. Jap. 43, 1970, 2632 (for the reaction of disulphides).

In the oxidation step, the compounds were oxidised to their corresponding sulphones. Preferred oxidising agents are peracids in an inert organic solvent or in a mixture of water and an organic solvent. Suitable peracids are, for example, peracetic acid, m-chloroperoxybenzoic acid (MCPBA) and monoperphthalic acid. Suitable solvents are chloroform, dichloromethane, tetrahydrofuran and ethanol.

It is to be understood that in the processes above any functional group, if needed or desired, can be masked by conventional methods and unmasked at the end or when convenient. Also, it is understood that a group R₄ can be converted by conventional methods into a different group R₄ included within those previously defined, if desired, at the end or at any stage of the process above. These conversions or masking/unmasking of protecting groups are well known on cephems II.

Compounds II and III are known compounds or can be prepared from known compounds by known methods.

The potentialities of protease inhibitor therapy in the treatment of conditions resulting from the destruction of connective tissues have recently received particular attention. Much effort has been devoted to the search for inhibitors of human leukocyte elastase (HLE) which is the primary destructive agent in pulmonary emphysema and is probably involved in rheumatoid arthritis (J. C. Power, Am. Rev. Resp. Diseases 127, S54-S58, 1983: C. H. Hassal et al., FEBS Letters, 183, n. 2, 201, 1985: G. Weinbaum and V. V. Damiano, TIPS, 8, 6, 1987: M. Velvart, Rheymatol, Int., 1, 121, 1981). Low molecular weight inhibitors appear to have a number of advantages over natural high molecular weight protease inhibitors from either plant or animal sources: 1) they can be obtained in quantities; 2) they can be rationally designed and optimized; 3) they are not antigenic: 4) they may be used orally or in aerosols. Many low molecular weight elastase inhibitors discovered so far contain reactive functional groups (chloromethyl ketones, isocyanates, etc.): they may react with functional groups of proteins, and therefore they may be quite toxic. In this respect β-lactam compounds are of potential interest because, though reactive towards serine protease, they are, as Ks known, non-toxic at very high concentrations.

The compounds of the present invention are characterized by hight levels of inhibitory activity on HLE. In particular, they favourably compares with the most active cephalosporanic esters and amides (Nature 1986, 33, 332, 192) for what concerns the rate of formation ($K_{on}$), the equilibrium constant ($k_{off}/k_{on}$), and the apparent dissociation constant of the HLE-inbibitor complex at steady state ($K_i^{ss}$). To illustrate this point, Table I reports the kinetic parameters referred to above, determined for some compounds of the present invention, in comparison with Merck S & D L-659, 286, a cephalosporanic compound reportedly undergoing preclinical studies (Am. Rev.Repir. Dis. 1988, 137, 204; Agents and Actions, 1988, 25, 60).

TABLE I

| Compound[a] | Kinetic parameters for HLE inhibition[c] | | |
|---|---|---|---|
| | $k_{on}$ ($10^4$ M$^-$ S$^{-1}$) | $k_{off}/k_{on}$ (nM) | $K_i^{ss}$ (nM) |
| Comp. 3 | 48 | 7.5 | 2.6 |
| Comp. 11 | 126 | 3 | 8.2 |
| Comp. 59 | 15 | 20 | 16 |
| Comp. 60 | — | — | 4.3 |
| L-659,286[b] | 0.15 | 2100 | 140 | a) Compound numbers identifying the structure are those reported in the list of preferred compounds and, in the Examples, indicated in brackets after the pertinent chemical name.

b) L-659,286, 7α-methoxy-8-oxo-3-[[1,2,5,6-tetrahydro-2-methyl-5,6-dioxo-1,2,4-triazin-3-yl]thio]-methyl-5-thia-1-aza-6R-bicyclo[4.2.0]oct-2-ene-2-pyrrolidine carboxamide-5,5-dioxide, was synthesized in our laboratories from 7-amino-3-desacetoxycephalosporanic acid. Its structural identity and purity ($\geq 95\%$) was fully confirmed by spectral and analytical data.

c) Kinetic parameters of HLE (Calbiochem, Lot 702038) inhibition were determined at 37° C., 0.027 M pH 7.4 phosphate buffer, 1% DMSO, 1% MeCN, NaCl (I=0.15), by monitoring the release of 7-amino-4-methylcoumarin (fluorescence detection) from N-methoxysuccinyl-alanylprolyl-valyl-7-amido-4- methylcoumarin as substrate, according to the equations:

$$[P] = V_s t + \frac{(Vz - Vs)}{K} \cdot (1 - e^{-kt})$$

$$k = k_{off} + \frac{k_{on} \cdot [I]}{1 + [S]/K_m}$$

$$V_s = V_o \cdot \frac{1 + [S]/K_m}{1 + [S]/K_m + [I]/K_i^{ss}}$$

wherein:

[P], [I], [S] = product, inhibitor and substrate concentration
$V_s$ = steady state rate
$V_z$ = zero time rate
$V_o$ = rate at [I]=O
$K_m$ = Michaelis constant for the enzyme-substrate pair (independently determined under the same experimental conditions).

Owing to their high elastase-inhibiting activity and their quite negligible toxicity, the compounds of the invention can be used to make medicaments useful to prevent or arrest the progression of diseases caused by proteolytic degradation of lungs and connective tissues, reduce inflammation and fever, and relieve pain. Such diseases include emphysema, acute respiratory distress syndrome, bronchial inflammation, rheumathoid arthritis, osteoarthritis, infectious arthritis, rheumatic fever, sphondylitis, gout, lupus and psoriasis.

Accordingly, the invention also provides a pharmaceutical or veterinary composition comprising a compound of the general formula I in admixture with a pharmaceutically or veterinarily acceptable diluent or carrier. The pharmaceutical or veterinary compositions according to the invention may be prepared in a conventional way in a variety of dosage forms and for various ways of administration. In particular, the compositions according to the invention may be administered:

a)

orally, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets Contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and distintegrating agents, for example maize starch, or alginic acid: binding agents, for example starch, gelatin or acacia, and lubricating agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl or n-propyl p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavouring agents may be added to provide a palatable oral preparation. These conditions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsion may also contain sweetening and flavouring agents.

Syrups and elixirs may be formulated with sweetening agents, for example glycerol, sorbitol or sucrose. Such formulations may also contain a demulcent, a preservative and flavouring and colouring agents.

b)

parenterally, either subcutaneously or intravenously, or intramuscularly, or intrasternally, or by infusion techniques, in the form of sterile injectable aqueous or oleagenous suspensions. The pharmaceutical compositions may be in the form of a sterile injectable aqueous or olagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables.

c)

by inhalation, in the form of aerosols or solutions for nebulizers;

d)

rectally, in the form of suppositories prepared by mixing the drug with a suitable non-irritating excipient which is solid at ordinary temperature but liquid at the rectal temperature and will therefore melt in the rectum to release the drug. Such materials are cocoa butter and polyethylene glycols;

e)

topically, in the form of creams, ointments, jellies, solutions or suspensions.

Daily doses are in the range of about 0.5 to about 100 mg per kg of body weight, according to the activity of the specific compound, the age, weight and conditions of the subject to be treated, the type and severity of the disease, and the frequency and route of administration; preferably, daily dosage levels for humans are in the range of 50 mg to 2 g. The amount of active ingredient that may be combined with the carrier materials to produce a single dosage form will vary depending upon the host treated and the particular mode of administration. For example, a formulation intended for the oral administration to humans, may contain from 5 mg to 2 g of active agent compounded with an appropriate and convenient amount of carrier material which may vary from about 5 to 95 percent of the total composition. Dosage unit forms will generally contain between from about 25 mg to about 500 mg of active ingredient.

The invention is illustrated by the following Examples.

EXAMPLE 1 t-Butyl 3-aceto xymethyl-7S-chloro-8-oxo-5-thia-1-azabicyclo[4,2,0 oct-2-ene-5,5-dioxide-2-carbothiolate

Compound 3

A solution of 5 g of (7α)-chlorocephalosporanic acid in 45 ml of dichloromethane and 15 ml of ethanol was stirred overnight with 8 g of m-chloroperoxybenzoic acid at 5° to 10° C. The reaction mixture was washed with aqueous sodium bisulphite and the solvent from the organic layer was removed in vacuo. The residue was dissolved in 40 ml of diethyl ether and stood overnight to crystallize. 2.8 g of 2-carboxy-3-acetoxymethyl-7S-chloro-8-oxo-5-thia-1-azabicyclo[4,2,0]oct-2-ene-5,5-dioxide were obtained a as a white powder.

323 g (1 mmol) of this material was sequentially treated at −20° C. with 0.6 ml of pyridine, 0.135 ml (1.2 mmol) of t-butyl mercaptan and 4 ml of polyphosphate ester (PPE; for its preparation see: W. Pollmann, G. Schramm, *Biochem. Biophys. Acta*, 80, 1 (1964)).

The reaction mixture was stood at 0° C. for 5 hours. It was then poured into a mixture of ethyl acetate and aqueous sodium bicarbonate solution and stirred vigorously. The organic phase was dried over anhydrous sodium sulphate, and concentrated in vacuo. Chromatography of the residue over silica gel (n-hexane:ethyl acetate mixtures as eluants) afforded the title product as a white powder (290 mg).

IR (KBr) υ max 1790, 1735, 1665, 1650 $cm^{-1}$

NMR (90 MHz, $CDCl_3$) δ ppm 1.60 (9H, s), 2.11 (3H, s), 3.92 (2H, ABq, J=18Hz), 4.81 (2H, ABq, J=14Hz), 4.85 (1H, d, J=2Hz), 5.37 (1H, d, J=2Hz)

EXAMPLE 2 n-Butyl 3-acetoxymethyl,7S-chloro-8-oxo-5-thia-1-azabicyclo[4,2,0]oct-2-ene-5,5-dioxide-2-carbothiolate

Compound 2

0.107 ml of n-butanethiol and 206 mg of dicyclohexylcarbodiimide were added, at room temperature, to a stirred solution of 323 mg of 2-carboxy-3-acetoxymethyl-7S-chloro-8-oxo-5-thia-1-azabicyclo[4,2,0]oct-2-ene-5,5-dioxide (see Example 1) in 12 ml of dichloromethane. After 10 minutes the solvent was removed under vacuum and the residue was purified by flash chromatography on silica, using n-hexane:ethyl acetate mixtures as eluants. The title product was obtained as a waxy solid (90 mg).

IR (KBr) υ max 1812, 1735, 1650 cm$^{-1}$

NMR(CDCl$_3$, 90 MHz) δ ppm 0.93 (3H, t, J=6.2Hz), 1.1–2.0 (4H, m), 2.11 (3H, s), 3.08 (2H, d, J=6.3Hz), 3.92 (2H, ABq, 17.5Hz), 4.83 (1H, d, J=1.8Hz), 4.84 (2H, ABq, J=14.5Hz), 5.34 (1H, d, J=1.8Hz)

MS(FD): 395 m/z (M+)

EXAMPLE 3 p-Methoxyphenyl 3-acetoxymethyl-7S-chloro-8-oxo-5-thia-1-azabicyclo[4,2,0]oct-2-ene-5,5-dioxide-2-carbothiolate

Compound 1

Following a similar procedure to that described in Example 2 but substituting p-methoxy-thiophenol for n-butanethiol, the title product was obtained as white powder (25% yield).

IR (KBr) υ max 1815, 1740, 1670 cm$^{-1}$

NMR (90 MHz, CDCl$_3$), δ ppm, 2.12 (3H, s), 3.87 (3H, s), 4.02 (2H, ABq, J=18Hz), 4.82 (2H, ABq, J=14.5Hz), 4.93 (1H, d, J<2Hz), 5.41 (1H, d, J<2Hz), 7.02 (2H, d, J=8Hz), 7.45 (2H, d, J=8Hz), MS(FD)=445 m/z (M+)

EXAMPLE 4

Following a procedure similar to that described in Example 1, and substituting the appropriate mercaptan for t-butylmercaptan, there were obtained:

Isopropyl 3-acetoxymethyl-7S-chloro-8-oxo-5-thia-1-azabicyclo[4,2,0]oct-2-ene-5,5-dioxide-2-carbothiolate

Compound 4

IR (KBr) υ max 1805, 1735, 1650, 1620 cm$^{-1}$

NMR (CDCl$_3$, 90 MHz) δ ppm, 1.41 (6H, d, J=6.5 Hz), 2.10 (3H, s), 3.7–4.0 (1H, m) 3.93 (2H, ABq, J=17.8 Hz), 4.83 (1H, d, J=1.6 Hz), 4.85 (2H, ABq, J=14.3 Hz), t-Butyldiphenylsilyloxyethyl 3-acetoxymethyl-7α-chloro-8-oxo-5-thia-1-azabicyclo[4,2,0]oct-2-ene-5,5-dioxide-2-carbothiolate

Compound 55

IF (KBr) υ max 1810, 1740, 1660 cm$^{-1}$

NMR (CDCl$_3$, 90 MHz) δ ppm, 1.07 (9H, s), 2.05 (3H, s), 3.28 (2H, t, J=6 Hz), 3.88 (2H, t, J=6 Hz), 3.95 (2H, ABq, J=18 Hz), 4.83 (2H, ABq, J=14.2 Hz), 4.86 (1H, d, J=1.7 Hz), 5.38 (1H, d, J=1.7 Hz), 7.3–7.6 (10H, m)

Benzyl 3-acetoxymethyl-7S-chloro-8-oxo-5-thia-1-azabicyclo-[4,2,0]oct-2-ene-5,5-dioxide-2-carbothiolate

Compound 11

IR (KBr) υ max 1812, 1738, 1655 cm$^{-1}$

NMR (90 MHz, CDCl$_3$), 2.07 (3H, s), 3.96 (2H, ABq, J=18.5 Hz), 4.32 (2H, s), 4.86 (2H, ABq, J=13.5 Hz), 4.87 (1H, d, J=1.8 Hz), 5.35 (1H, d, J=1.8 Hz), 7.37 (5H, s)

Diphenylmethoxycarbonylmethyl 3-acetoxymethyl-7S-chloro-8-oxo-5-thia-1-azabicyclo[4,2,0]oct-2-ene-5,5-dioxide-2-carbothiolate

Compound 56

IR (KBr) υ max 1808, 1740, 1665 cm$^{-1}$

NMR (CDCl$_3$, 90 MHz), 2.07 (3H, s), 3.93 (2H, ABq, J=18 Hz), 3.97 (2H, s), 4.80 (2H, ABq, J=14.5 Hz), 4.80 (1H, d, J=1.7 Hz), 5.34 (1H, d, J=1.7 Hz), 6.93 (1H, s), 7.39 (10H, s)

2-Diphenylmethoxycarbonyl-2-(t-butoxycarbonylamino)-ethyl 3-acetoxymethyl-7S-chloro-8-oxo-5-thia-1-azabicyclo[4,2,0]oct-2-ene-5,5-dioxide-2-carbothiolate

Compound 57

IR (KBr) υ max 1807, 1738, 1710 (br), 1660 ( sh. ) cm$^{-1}$

NMR (CDCl$_3$, 200 MHz), 1.41 (9H, s), 2.08 (3H, s), 3.38 (1H, dd, J=5.5 and 14.1 Hz), 3.73 (1H, d, J=18.2 Hz), 3.86 (1H, dd, J=4.3 and 14.1 Hz), 4.00 (1H, d, J=18.2 Hz), 4.54 (1H, d, J=14.0 Hz), 4.78 (1H, m), 4.79 (1H, m), 5.03 (2H, d, J=14.0 Hz), 5.33 (1H, d, J=1.7 Hz), 6.90 (1H, s), 7.33 (10H, s)

EXAMPLE 5

2-Hydroxyethyl 3-acetoxymethyl-7S-chloro-8-oxo-5-thia-1-azabicyclo[4,2,0]oct-2-ene-5,5-dloxide-2-carbothiolate

Compound 19

300 ml of acetic acid and 250 mg of tetrabutylammonium fluoride trihydrate were added sequentially, at room temperature, to a stirred solution of 60 mg of 2-t-butyldiphenylsilyloxymethyl 3-acetoxymethyl-7S-chloro-8-oxo-5-thia-1-azabicyclo[4,2,0 oct-2-ene-5,5-dioxide-2-carbothiolate in 6 ml of dry tetrahydrofuran. The resulting solution was stood for 20 hours. Removal of the solvent and flash chromatography of the residue afforded the title product (25 mg).

NMR (90 MHz, CDCl$_3$), 2.10 (3H, s), 3.27 (2H, m), 3.85 (2H, m), 3.91 (2H, ABq, J=18 Hz), 4.81 (2H, ABq, J=14 Hz), 4.87 (1H, d, J=1.6 Hz), 5.36 (1H, d, J=1.6 Hz)

EXAMPLE 6

2-Amino-2-carboxyethyl 3-acetoxymethyl-7S-chloro-8-oxo-5-thia-1-azabicyclo[4,2,0]oct-2-ene-5,5-dioxide-2-carbothiolate

Compound 34

A solution of 120 mg of 2-diphenylmethoxycarbonyl-2-(t-butoxycarbonylamino)ethyl-7S-chloro-8-oxo-5-thia-1-azabicyclo[4,2,0]oct-2-ene-5,5-dioxide-2-carbothiolate in 8 ml of dichloromethane and 1 ml of anisole was treated with 1 ml of trifluoroacetic acid and stood for 5 hours. After removal of the solvent, the residue was treated with 15 ml of dichloromethane and 5 ml of diisopropyl ether and stirred for ten minutes at room temperature. Centrifugation of the suspension afforded a white powder (42 mg)

IR (KBr) υ max 1808, 1742, 1670, 1620 cm$^{-1}$

NMR (DMSO-D$_2$O, 200 MHz), 5.92 (1H, d, J=1.6 Hz), 5.66 (1H, d, J=1.6 Hz), 4.70 (2H, ABq, J=13.6 Hz). 3.74 (1H, m), 3.66 (2H, s, obscured), 3.52 (1H, dd, J=5.2 and 13.8 Hz), 3.35 (1H, dd, J=6.6 and 13.8 Hz), 2.01 (3H, s)

EXAMPLE 7

Carboxymethyl 3-acetoxymethyl-7S-chloro-8-oxo-5-thia-1-azabicyclo[4,2,0]oct-2-ene-5,5-dioxide-2-carbothiolate Compound 22

180 mg of diphenylmethoxycarbonylmethyl 3-acetoxymethyl-7S-chloro-8-oxo-5-thia-1-azabicyclo[4,2,0]oct-2-ene-5,5-dioxide-2-carbothiolate was dissolved in 25 ml of a mixture of dichloromethane-anisole-trifluoroacetic acid (8:1:1 by volume) and left at room temperature for 2.5 hours. Removal of the solvent gave a residue which was chromatographed on silica gel (n-hexane:ethyl acetate mixtures as eluants). The title product was obtained as a white powder (105 mg)

IR (KBr) $v$ max 1810–1815, 1720–1740, 1655 cm$^{-1}$

NMR (DMSO, 200 MHz),2.03 (3H, s), 3.88 (2H, s), 4.42 (2H, ABq, J=18.0 Hz), 4.70 (2H, ABq, J=13.5 Hz), 5.72 (1H, d, J=1.5 Hz),

EXAMPLE 8

2-Phenylethyl 3-acetoxymethyl-7S-chloro-8-oxo-5-thia-1-azabicyclo[4,2,0]oct-2,ene-5,5-dioxide-2-carbothiolate Compound 15

Pyridine (0.6 ml) and 2-phenylethylmercaptan (0.14 ml) were added to a solution of 3-acetoxymethyl-2-carboxy-7S-chloro-8-oxo-5-thia-1-azabicyclo [4,2,0]oct-2-ene 5,5-dioxide (0.323 g) or dichloromethane (4ml). Polyphosphate ester (PPE), 4 ml, was then added at −10° C. and the reaction mixture was stirred at −10° C. for 6 hours.

After partitioning between ethyl acetate and aqueous sodium bicarbonate solution, the organic phase was collected, dried over anhydrous sodium sulphate, and concentrated in vacuo. The residue was chromatographed over silica gel (n-hexane: ethyl acetate) and the faster-running product was collected. This material (0.13 g) was dissolved in dichloromethane (20 ml) and treated at −40° C. with 70% m-chloroperoxybenzoic acid (0.11 g). The mixture was stirred at −10° C. for 1 hour and then sequentially washed with aqueous bisulphite and aq. bicarbonate solutions.

The organic phase was dried and concentrated in vacuo. Chromatography of the residue over silica gel (n-hexane/ethyl acetate) afforded the title compound as a white solid (80 mg); m.p. 133°–135° C.

IR (KBr) $v_{max}$ 1815, 1730, 1640 cm$_{-1}$

NMR (CDCl$_3$, 90 MHz) δ ppm, 2.10 (3H, S), 3.0 and 3.30 (4H, each d, J=7 Hz), 3.75 and 4.05 (2H, each d, J=18 Hz), 4.65 and 4.97 (2H each d, J=14 Hz), 4.81 (1H, d, J=1.8 Hz), 5.35 (1H, d, J=1.8 Hz), MS(FD)=443(M+), 384(—CH$_3$CO$_2$) m/z

EXAMPLE 9 t-Butyl 7S-chloro-3-methyl-8-oxo-5-thia-1-azabicyclo-[4,2,0]oct-2-ene-5,5-dioxide-2-carbothiolate Compound 58

A solution of 7α-chlorodesacetoxycephalosporanic acid (20 g) in methanol: water (1:1, 800 ml) was treated with potassium peroxymonosulphate (Oxone, Aldrich-Chemie GmbH) (90 g). After 105 minutes at 55° C., the reaction mixture was cooled and filtered from EtOAC-insoluble materials. The filtrate was partitioned between EtOAc-H$_2$O, and the organic phase was collected, washed with water, (200 ml), dried and concentrated to obtain crude 2-carboxy-7S-chloro-3-methyl-8-oxo-5-thia-1-azabicyclo [4,2,0]oct-2-ene 5,5-dioxide as a yellowish oil (15 g).

A portion of this material (3.2 g) in dichloromethane (40 ml) was treated with t-butylmercaptan (1.35 ml) and PPE (40 ml) according to the experimental procedure described in Example 1, thereby obtaining the title compound (1.7 g) as a white powder.

IR (KBr) $v_{max}$ 1800, 1660 cm$^{-1}$

NMR (90 MH$^z$, CDCl$_3$) δ ppm, 1.55 (9H,S), 2.07 (3H,S), 3.77 (2H, ABq, J=18 Hz), 4.73 (1H,d, J=1.5 Hz), 5.32 (1H, d, Y=1.5 Hz), MS (FD)=337 (M+), 280(—C$_4$H$_9$), 248(—SC$_4$H$_9$)m/z

EXAMPLE 10 t-Butyl 7S-chloro-3-methoxymethyl-8-oxo-5-thia-1-azabicyclo[4,2,0]oct-2-ene-5,5-dioxide-2-carbothiolate Compound 59

A solution of crude 7α-chlorocephalosporanic acid (10 g) in methanol (110 ml) and water (50 ml) was treated with an aqueous sodium bicarbonate solution(2.7 g in 120 ml). Calcium chloride (187 g) was added, and the reaction mixture was heated at 70° C. for 1.5 hours. After cooling to 10° C., conc. HCl was added (7 ml), and the solution extracted with ethyl acetate (2×350 ml). The extracts were washed with brine, dried (Na$_2$SO$_4$) and concentrated in vacuo. The residue was taken up in ethyl ether (150 ml) and stirred for 30 min. The insoluble material, mainly 7α-chlorocephalosporanic lactone, was discarded. The solution was concentrated to afford 2-carboxy-3-methoxymethyl-7S-chloro-8-oxo-5-thia-1-azabicyclo [4,2,0]oct-2-ene as a yellowish oil (4 g). A portion of this material (3.5 g) in 50% aqueous methanol (120 ml) was treated with potassium peroxymonosulphate (14 g) at 60° C. for 90 minutes.

After concentration in vacuo, the reaction mixture was partitioned between ethyl acetate: water.

Evaporation of the solvent from the organic extract left crude 2-carboxy-3-methoxymethyl-7S-chloro-8-oxo-5-thia-1-azabicyclo [4,2,0]oct-2-ene-5,5-dioxide (3 g) as a foam. A portion of this material (295 mg) was treated with t-butylmercaptan and PPE according to the experimental procedure described in Example 1, thereby obtaining the title compound (120 mg) as a white powder.

IR (KBr) $v_{max}$ 1790, 1665 cm$^{-1}$

NMR (90 MHz, CDCl$_3$) δ$_{ppm}$, 1.55 (9H, s), 3.35 (3H, S), 3.96 (2H, AB, J=16.5 Hz, 4.17 (2H, S), 4.80 (1H, d, J=1.8 Hz, 5.34 (1H, d, J=1.8 Hz)

EXAMPLE 11 t-Butyl 7S-chloro-3-(1-methyl-1,2,3,4-tetrazol-5-yl) thiomethyl-8-oxo-5-thia-1-azabicyclo[4,2,0]oct-2-ene-5,5-dioxide-2-carbothiolate Compound 60

A solution of 7α-chlorocephalosporanic acid sulphone (400 mg) in acetonitrile (15 ml) was treated with 5-mercapto-1-methyl-1,2,3,4-tetrazole (200 mg) and boron trifluoride etherate (0.5 ml). After 6 hours at 50° C., the reaction mixture was evaporated in vacuo, thereby obtaining crude 2-carboxy-7S-chloro-3-(1-methyl-1,2,3,4-tetrazol-5-yl) thiomethyl-8-oxo-5-thia-1- azabicyclo[4,2,0]oct-2-ene-5,5-dioxide as an amorphous solid.

Treatment of this material with t-butylmercaptan and PPE according to the experimental procedure described in Example 1 afforded the title compound as an amorphous solid, 110 mg.

IR (KBr) $v_{max}$ 1810, 1655 cm$^{-1}$

NMR (90 MHz, CDCl$_3$) $\delta_{ppm}$, 1.55 (9H, s), 3.98 (3H, s), 4.1–4.5 (4H, two ABq), 4.87 (1H, J=1.7 H$_z$), 5.35 (1H, J=1.7 H$_z$), MS(FD)=451 (M+), 394 (—C$_4$H$_9$) m/z

EXAMPLE 12 t-Butyl 3-(1-methyl-1,2,3,4-tetrazol-5-yl)thiomethyl-8-oxo-5-1-azabicyclo[4,2,0]oct-2-ene-5,5-dioxide-2-carbothiolate Compound 62

A solution of 7-aminodesacetoxycephalosporanic acid (7-ADCA) (42.9 g) in methanol (1.2 l) was sequentially treated at −15° C. internal temperature with 48% aqueous HBr (70 ml), 70% aqueous HClO$_4$ (115 ml), and aqueous sodium nitrite (35 g in 100 ml).

The mixture was vigorously stirred for 35 minutes, while the internal temperature was let rise from −15° C. to +20° C. Water (1.5 l) and ethylether (0.8 l) were added and the organic phase was separated, washed with brine (0.4 l), dried over Na$_2$SO$_4$ and concentrated in vacuo, thereby obtaining crude 7S-bromo-2-carboxy-3-methyl-8-oxo-5-thia-1-azabicyclo[4,2,0]oct-2-ene as a yellow syrup.

This material was oxidized with potassium peroxymonosulphate (1.7 mol equiv.) according to the procedure described in Example 9. The resulting crude material was dissolved in dichloromethane (200 ml) and acetic acid (20 ml) and treated portionwise with Zn dust (30 g) under stirring for 1 hour. The reaction mixture was filtered and partitioned between dichloromethane and water. The aqueous phase was made acidic with conc. HCl, satured with NaCl and extracted with ethyl acetate. Evaporation of the solvent left a yellowish solid, which was taken up with ethyl ether and filtered. The collected product was dissolved in ethanol-free dichloromethane and treated with oxalyl chloride (4.6 ml) under DMF catalysis (0.05 ml) at 0° C. for 2 hours.

The reaction mixture was evaporated under high vacuum and taken up again in dichloromethane. Tert-butanol (30 ml) was added, followed by triethylamine (4 ml). After 15 minutes the solution was washed with aqueous sodium bicarbonate. The organic layer was dried (Na$_2$SO$_4$) and the solvent removed in vacuo. Silica gel chromatography (hexane:ethyl acetate mixtures) afforded in this sequence, t-butyl 7S-methoxy-3-methyl-8-oxo-5-thia-1-azabicyclo[4,2,0]oct-2-ene-5,5-dioxide-2-carboxylate (0.75 g), and t-butyl 3-methyl-8-oxo-5-thia-1-azabicyclo[4,2,0]oct-2-ene-5,5-dioxide-2-carboxylate (9.2 g).

A portion of the latter compound (0.7 g) dissolved in carbon tetrachloride (50 ml), was heated for 4 hours at reflux temperature with N-bromosuccinimide (0.86 g) and azo-bis-isobutyronitrile (AIBN, 15 mg). The reaction mixture was diluted with dichloromethane and vigorously stirred for 15 minutes with saturated sodium bisulphite solution.

The organic layer was collected, dried (CaCl$_2$) and concentrated. Silica gel chromatography afforded t-butyl 3-bromomethyl-8-oxo-5-thia-1-azabicyclo[4,2,0]oct-2-ene-5,5-dioxide-2-carboxylate (0.55 g). This compound was dissolved in acetonitrile and treated with 5-mercapto-1-methyl-1,2,3,4-tetrazole (0.19 g). After 10 minutes the solvent was removed in vacuo. Silica gel chromatography afforded t-butyl 3-(1-methyl-1,2,3,4-tetrazol-5-yl)thiomethyl-8-oxo-5-thia-1-azabicyclo[4,2,0]oct-2-ene-5,5-dioxide-2-carboxylate (400 mg) as a white solid. This compound was dissolved in a mixture of trifluoroacetic acid, dichloromethane and anisole (1:1:0.5).

After 30 minutes, the solution was concentrated and the residue taken up in dichloromethane (5 ml). After cooling to −20° C., pyridine (0.7 ml), t-butyl mercaptan (0.16 ml) and PPE (5 ml) were added, and the mixture left standing at 0° C. for 5 hours.

Workup and chromatography as described in Example 1 afforded the title compound as a yellowish powder (120 mg).

IR (KBr) $v_{max}$ 1807, 1638 cm$^{-1}$

NMR (90 MHz, CDCl$_3$) $\delta_{ppm}$, 1.53 (9H, s), 3.48 and 3.55 (1h, each d, J=4.9 Hz), 3.59 and 3.67 (1H, each d, J=2.5 Hz), 3.93 (3H, s), 3.98 (1H, d, J=17 Hz), 4.24 (1H, dd, J=17 and 0.9 Hz), 4.02 and 4.33 (2H, each d, J=14 Hz), 4.76 (1H, m)

EXAMPLE 13 t-butyl 7S-methoxy-3-(1-methyl-1,2,3,4-tetrazol-5-yl)thiomethyl-8-oxo-5-thia-1-azabicyclo[4,2,0]oct-2-ene-5,5-dioxide-2-carbothiolate Compound 61

A solution of t-butyl 7S-methoxy-3-methyl-8-oxo-5-thia-1-azabicyclo[4,2,0]oct-2-ene-5,5-dioxide-2-carboxylate (800 mg) in carbon tetrachloride (100 ml) was treated with NBS (550 mg) and AIBN (50 mg), and then heated for 3 hours at reflux temperature. The reaction mixture was concentrated in vacuo and the residue fractionated by silica gel chromatography, collecting t-butyl-3-bromomethyl-7S-methoxy-8-oxo-5-thia-1-azabicyclo[4,2,0]oct-2-ene-5,5-dioxide-2-carboxylate (700 mg) as a syrup.

This material was dissolved in acetonitrile (20 mg) and DMF (5 ml). After addition of 5-mercapto-1-methyl-1,2,3,4 tetrazole (500 mg), the mixture was stirred for 10 min, most of the solvent was removed in vacuo, and the residue partitioned between ethyl acetate and water. The organic phase was dried (Na$_2$SO$_4$), concentrated, and the residue was purified by silica gel chromatography, obtaining t-butyl 7S-methoxy-3-(1-methyl-1,2,3,4-tetrazol-5-yl)thiomethyl-8-oxo-5-thia-1-azabicyclo[4,2,0]oct-2-ene-5,5-dioxide-2-carboxylate as a solid (605 mg); MS (FD) 431 (M+)m/z.

This compound was dissolved in a mixture of trifluoroacetic, dichloromethane and anisole (1:1:0.5).

After 30 min., the solution was concentrated in vacuo and the residue was triturated with ethyl ether.

Filtration afforded 2-carboxy-7S-methoxy-3-(1-methyl-1,2,3,4-tetrazol-5-yl)thiomethyl-8-oxo-5-thia-1-azabicyclo[4,2,0]oct-2-ene-5,5-dioxide(400 mg) as a light tan powder.

This compound dissolved in dichloromethane, was treated at −20° C. with pyridine (0.5 ml), t-butyl mercaptan (0.135 ml) and PPE (3.5 ml), and then allowed to react for 5 hours at 0° C. Workup and chromatography as described in Example 1 afforded the title product (250 mg).

IR (CHCl$_3$) $v_{max}$ 1800, 1650 cm$^{-1}$

NMR (90 MHz, CDCl$_3$) $\delta_{ppm}$, 1.55 (9H, s), 3.58 (3H, s), 3.88 (1H, d, J=17.5 Hz), 3.93 (3H, s), 4.04 and 4.38 (2H, each d, J=14 Hz), 4.27 (1H, dd, J=17.5 and 1.1

Hz), 4.63 (1H, dd, J=1.7 and 1.1 Hz), 5.13 (1H, d, J=1.7 Hz),

EXAMPLE 14

2-Diphenylmethoxycarbonyl-2-(t-butoxycarbonylamino)ethyl 7S-methoxy-3-(1-methyl-1,2,3,4-tetrazol-5-yl)thiomethyl-8-oxo-5-thia-1-azabicyclo[4,2,0]oct-2-ene-5,5-dioxide-2-carbothiolate Compound 105

A dichloromethane solution of 2-carboxy-7S-methoxy-3-(1- methyl-1,2,3,4-tetrazol-5-yl)thiomethyl-8-oxo-5-thia-1-azabicyclo[4,2,0]oct-2-ene-5,5-dioxide, prepared as described in Example 13, was allowed to react with pyridine, N-tert-butoxycarbonyl-L-cysteine benzhydril ester, and PPE, according to the general experimental conditions described in Example 1.

The title material was thereby obtained (75% after silica gel chromatography) as a yellowish oil;
IR(CHCl$_3$) $\nu_{max}$ 1800, 1735, 1705, 1665 cm$^{-1}$
NMR (CDCl$_3$, 200 MHz) $\delta_{ppm}$, 1.39 (9H,s), 3.36 (1H, dd, J=6.8 and 14.1 H$_z$), 3.87 (1H, dd, J=4.1 and 14.1 H$_z$), 3.90 (1H, d, J=17.2 H$_z$), 3.94 (1H, d, J=14.5 H$_z$), 4.23 (1H, d, J=17.2 H$_z$), 4.53 (1H, br, H$_6$), 4.59 (1H, d, J=14.5 H$_z$), 4.7 (1H, m, cysteine C$_\alpha$), 5.13 (1H, d, J=1.6 H$_z$, H$_z$), 5.75 (1H, J=8.1 H$_z$, exch D$_2$O), 6.90 (1H, s), 7.27-7.35 (10 H, m)

We claim:

1. A compound of formula I

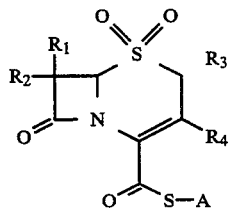

wherein

A represents
(a) a hydrogen atom,
(b) a straight chain or branched chain alkyl group having from 1 to 20 carbon atoms,
(c) a straight chain or branched chain alkenyl group having from 2 to 10 carbon atoms,
(d) an C$_{6-10}$ aryl group,
(e) a cycloalkyl group being of monocyclic, bicyclic or bridged ring form and having from 3 to 10 carbon atoms,
(f) an aralkyl group in which the aryl part is as defined in (d) above and the alkyl part is as defined in (b) above,
(g) a cycloalkylalkyl group in which the cycloalkyl part is as defined in (e) above and the alkyl part is as defined in (b) above, each of the groups defined in (b) to (g) above being unsubstituted or substituted by one or more of
(i) a halogen atom,
(ii) an amino or a group of the formula NHR$_a$, NR$_a$R$_b$, NHCOR$_c$, NHCOOR$_c$ or NHSO$_2$R$_a$ wherein each of R$_a$ and R$_b$ independently represents a straight chain or branched chain alkyl group having from 1 to 7 carbon atoms, or said alkyl group substituted by a carboxy group, a phenyl group or a benzyl group and R$_c$ represents a 2-carboxyethyl or 3-carboxypropyl group or any of the groups which R$_a$ may represent,
(iii) a group of the formula COR$_d$, COOR$_d$, CO$_2$CH$_2$— —COR$_d$ or CONHR$_d$ wherein R$_d$ represents a hydrogen atom, a 2-carboxy-2-aminoethyl or diphenylmethyl group or any of the groups which R$_c$ may represent or
(iv) as a ring substituent only, a straight chain or branched chain alkyl, alkenyl or alkynyl group each of which has up to 4 carbon atoms and is optionally substituted by a carboxy group or a cycloalkyl group having from 3 to 6 carbon atoms;

R$_1$ represents
(1) a fluorine, chlorine, bromine or iodine atom
(2) a group A as above defined, or
(3) a group OA wherein A is as above defined;

R$_2$ represents hydrogen;

R$_3$ represents a hydrogen atom or a methyl group, and

R$_4$ represents
(1) a group A as above defined,
(2) a group CH$_2$OA wherein A is as above defined,
(3) a group CH$_2$SA, CH$_2$SOA or CH$_2$SO$_2$A wherein A is as above defined,
(4) a group CH$_2$OCOA or CH$_2$OZ wherein A and Z are as above defined, or a salt thereof with a pharmaceutically acceptable anion or cation.

2. A compound according to claim 1 in which A represents
(a') a hydrogen atom,
(b') a straight chain or branched chain alkyl group having from 1 to 20 carbon atoms,
(d') a phenyl or naphthyl group
(e') a cycloalkyl group being of monocyclic, bicyclic or bridged ringform and having from 3 to 10 carbon atoms,
(f') a phenylalkyl or naphthylalkyl group in which the alkyl part is as defined in (b') above,
(g') a cycloalkylalkyl group in which the cycloalkyl part is as defined in (f') above and the alkyl part is as defined in (b') above, each of the groups defined in (b') to (g') above being unsubstituted or substituted by one or more of
(i') a halogen atom,
(ii') amino or a group of the formula NHR$_e$, NR$_e$R$_f$, NHCOR$_g$, NHCOOR$_g$ or NHSO$_2$R$_e$ wherein each of R$_e$ and R$_f$ independently represents a straight chain or branched chain alkyl group having from 3 to 7 carbon atoms, a phenyl group or a benzyl group and R$_g$ represents a 2-carboxyethyl or 3-carboxypropyl group or any of the groups which R$_e$ may represent,
(iii') a group of the formula

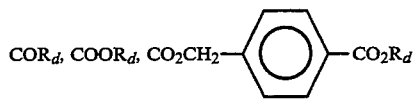

or CONHR$_d$
wherein R$_d$ is as above defined, or
(iv') as a ring substituent only, a straight chain or branched chain alkyl group having from 1 to 4 carbon atoms.

3. A compound according to claim 1 in which A represents a hydrogen atom or a methyl, ethyl, propyl, isopropyl, butyl, s-butyl, t-butyl, pentyl, neopentyl, hexyl, cyclopropyl, cyclopentyl, cyclohexyl, adamantyl, phenyl, benzyl, naphthyl, o-tolyl, o,o-xylyl, diphenylmethyl, trityl, 1-phenyl-2-propyl, 1-phenylethyl, phenethyl, 4-carboxybenzyl, 3-carboxybenzyl, carboxymethyl, 1-carboxyethyl, 2-carboxypropyl, 4-carboxyphenyl, [hydroxyethyl, 2-(t-butyoxy)ethyl, 2-pivaloyloxyethyl, 2-acetoxyethyl, 2-pyridiniumethyl, 4-methoxyphenyl, 2-pyridyl, 2-(3-carboxypropionyloxy)-ethyl, 2-carboxymethoxy-ethyl, 2-(carboxyethylcarbamoyloxy)-ethyl, 2(3-carboxy-3-aminopropionyloxy)-ethyl,]2-carboxy-2-aminoethyl, 3-carboxy-3-aminopropyl, 2-carboxy-2-amino-1methylethyl, 4-(t-butoxycarbonyl)-benzyl, [t-butyldiphenylsilyloxyethyl,]2-diphenylmethoxy-carbonyl-2-(t-butoxycarbonylamino)-ethyl, 2-(t-butoxycarbonylamino)-2carboxyethyl, t-butoxycarbonylmethyl, 2-t-butoxycarbonylbenzyl-2-(t-butoxycarbonylamino-ethyl, or 2-(t-butoxycarbonylamino)-2-t-butoxycarbonylethyl group.

4. A compound according to claim 1 in which $R_1$ represents a fluorine, chlorine or bromine atom, a methyl, ethyl, formamido, acetamido or trifluoroacetamido group, or a group NH-Ala, NH-Ala(acetyl), NH-Val(3-carboxypropionyl), NH-L-Pro-L-Val, NH-Lys(3-carboxypropionyl), NH-Pro-Ala-Ala or NH-Pro-Ala-Ala(acetyl) group.

5. A compound according to claim 1 in which $R_4$ represents a methyl, bromomethyl, acetoxymethyl, hydroxymethyl, carbamoyloxymethyl, methoxy methyl, phenoxymethyl, aminomethyl, pyridinium- methyl, 4-carboxymethylpyridiniummethyl, benzoyloxymethyl, benzoxy- methyl, 3-pyridyloxymethyl, phenacetoxymethyl, methyl- sulphonylmethyl, phenylsulphinylmethyl 3-carboxy- propionyloxymethyl, 4-carboxyenzoyloxymethyl, 4-(t -butoxycarbonyl)benzoyloxymethyl, N-(carboxymethyl) -carbamoyloxymethyl or (1-carboxy-2-methyl-propylamino)- methyl group; a group $CH_2NH$—Val: a group $CH_2O$—Val, $CH_2$—O—Ala, $CH_2$—O—Gly or $CH_2$—O—Pro—Val or an Ac, Boc or Cbz protected derivative of such a group; a group $CH_2$—O—Ala(Glu): a group $CH_2$—O—CONH—CH(Rp)COOH wherein $R_p$ represents a straight chain or branched chain alkyl group having from 3 to 7 carbon atoms or a phenyl group; a group

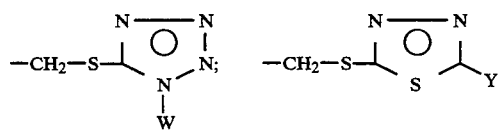

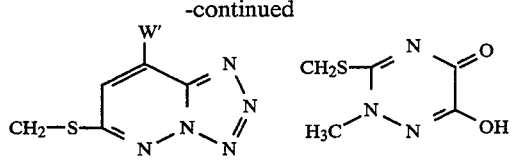

in which W represents hydrogen atom, methyl or $(CH_2)_nCO_2H$ group, n is 1, 2 or 3, Y represents a methyl, carboxymethylthio or carboxymethyl group and W' represents hydrogen atom or carboxy group; or a group

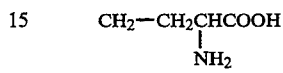

or its Ac Boc or Cbz protected derivative and/or its methyl, ethyl, t-butyl, benzyl or diphenylmethyl ester.

6. A pharmaceutical or veterinary composition for use in preventing or arresting the progression of a disease caused by proteolytic degradation of the lungs and connective tissues, in reducing inflammation or fever or in relieving pain, said composition comprising an effective amount of a compound of formula I or a pharmaceutically acceptable salt thereof according to claim 1 in admixture with a pharmaceutically or veterinarily acceptable diluent or carrier.

7. A method of preventing or arresting the progression of a disease caused by proteolytic degradation of the lungs and connective tissue, of reducing inflammation or fever or of relieving pain in a host, which method comprises administering to the said host an effective amount of a compound of formula I or a pharmaceutically acceptable salt thereof according to claim 1.

8. A compound according to claim 1, in which A is said alkyl group (b), said aralkyl group (f), said alkyl group (b) substituted with said (ii) group or said (iii) group.

9. A compound according to claim 1, in which $R_1$ is fluorine, chlorine, bromine or iodine.

10. A compound according to claim 1, wherein $R_1$ is said group (A).

11. A compound according to claim 10, wherein $R_1$ is said $C_{1-20}$alkyl group (b), said $C_{2-10}$alkenyl group (c) or said $C_{6-10}$aryl group (d).

12. A compound according to claim 1, wherein $R_1$ is said group (OA).

13. A compound according to claim 12, wherein $R_1$ is said group OA and A is said $C_{2-10}$; alkenyl group (b).

14. A compound according to claim 1, wherein $R_4$ is said group A.

15. A compound according to claim 14, wherein $R_4$ is said $C_{2-10}$alkenyl group (b).

16. A compound according to claim 1, wherein $R_4$ is said group $CH_2OA$.

17. A compound according to claim 1, wherein $R_4$ is said group $CH_2SA$, $CH_2SOA$ or $CH_2SO_2A$.

18. A compound according to claim 1, wherein $R_4$ is said group $CH_2OCOA$ or $CH_2OZ$.

* * * * *

UNITED STATES PATENT AND TRADEMARK OFFICE
CERTIFICATE OF CORRECTION

PATENT NO. : 5,356,888
DATED : October 18, 1994
INVENTOR(S) : Marco ALPEGIANI, et al.

It is certified that error appears in the above-indentified patent and that said Letters Patent is hereby corrected as shown below:

On the title page, Item [63] and Column 1, Lines 6 and 7, the PCT Information has been omitted and should read as follows:

--Continuation of Ser. No. 457,812, Jan. 12, 1990, abandoned, filed as PCT/EP89/00505, May 8, 1989--

Signed and Sealed this

Ninth Day of May, 1995

*Attest:*

BRUCE LEHMAN

*Attesting Officer*  *Commissioner of Patents and Trademarks*